United States Patent [19]

Kenna

[11] Patent Number: 5,037,423

[45] Date of Patent: Aug. 6, 1991

[54] METHOD AND INSTRUMENTATION FOR THE REPLACEMENT OF A KNEE PROSTHESIS

[75] Inventor: Robert V. Kenna, Saddle River, N.J.

[73] Assignee: Pfizer Hospital Products Group, Inc., New York, N.Y.

[21] Appl. No.: 520,483

[22] Filed: May 7, 1990

Related U.S. Application Data

[62] Division of Ser. No. 545,714, Oct. 26, 1983, Pat. No. 4,944,760.

[51] Int. Cl.[5] .............................................. A61B 17/55
[52] U.S. Cl. ...................................... 606/88; 606/86; 606/87; 606/89; 606/96
[58] Field of Search ...................... 606/88, 86, 87, 89, 606/96; 407/4; 408/116; 623/16, 18, 20, 23

[56] References Cited

U.S. PATENT DOCUMENTS

| | | | |
|---|---|---|---|
| 4,474,177 | 10/1984 | Whiteside | 606/88 |
| 4,567,886 | 2/1986 | Peterson | 606/88 |
| 4,653,488 | 3/1987 | Kenna et al. | 606/88 |
| 4,703,751 | 11/1987 | Pohl | 606/87 |
| 4,721,104 | 1/1988 | Kaufman et al. | 606/88 |
| 4,736,737 | 4/1988 | Fargie et al. | 606/88 |
| 4,907,578 | 4/1990 | Petersen | 606/88 |

Primary Examiner—David J. Isabella
Assistant Examiner—Anthony P. Zuttarelli
Attorney, Agent, or Firm—Peter C. Richardson; Lawrence C. Akers; Raymond W. Augustin

[57] ABSTRACT

A novel method for replacing a previously implanted knee joint prosthesis in a patient is disclosed in which the previously implanted femoral component is replaced with a revision femoral component having thicker distal and posterior bearing portions so as to restore the natural anatomic transverse joint plane and collateral ligamentous balance in extension and flexion of the prosthetic joint. Instrumentation for use in this method includes a novel revision cutting jig which is used in the preparation of the distal end of the femur for the implantation of the revision femoral component.

6 Claims, 9 Drawing Sheets

METHOD AND INSTRUMENTATION FOR THE REPLACEMENT OF A KNEE PROSTHESIS

This is a division, of application Ser. No. 06/545,714, filed on Oct. 26, 1983, now U.S. Pat. No. 4,944,760.

BACKGROUND OF THE INVENTION

Primary total knee arthroplasty, in which the natural femoral and tibial condylar bearing surfaces are replaced for the first time with prosthetic femoral and tibial components, has been practiced for many years with a high rate of success using a variety of different designs for the primary femoral and tibial components. It is usually preferred, if possible, to preserve the lateral and medial collateral ligaments during primary total knee arthroplasty and implant non-linked femoral and tibial components in order to preserve the stability and freedom of motion of the repaired joint. Examples of non-linked primary components highly suitable for use in cases in which the surgeon is able to preserve functioning lateral and medial collateral ligaments are disclosed in U.S. Pat. Nos. 3,728,742; 4,081,866; 4,209,861 and in the copending, commonly assigned U.S. patent application Ser. No. 350,130, filed Feb. 18, 1982, entitled "Bone Prosthesis with Porous Coating", now U.S. Pat. No. 4,550,448. In a rare number of cases, usually associated with improper surgical alignment of the primary components or the development after primary arthroplasty of severe conditions of arthritis or infection at the knee joint, it may become necessary to replace the originally implanted primary prosthetic components with a set of replacement femoral and tibial components, i.e. to practice revision total knee arthroplasty.

Revision total knee arthroplasty necessarily involves the removal of additional bone tissue (beyond the bone tissue removed for the primary arthroplasty) from the distal end of the femur (including the posterior region thereof) and the proximal end of the tibia in the preparation of these bones for implantation of the revision components. Prior to the present invention, the usual practice in cases in which the collateral ligaments are preserved has been to implant a primary type of femoral component having a spaced pair of bearing members as the revision component and to restore the full natural length of the patient's leg in extension by utilizing an appropriately-dimensioned revision tibial component having a spaced pair of bearing members that are much thicker than those of the replaced primary tibial component. The effect of this prior art practice is to shift the transverse joint plane, the horizontal plane passing through the lateral and medial component contact areas, in a proximal direction with respect to the normal anatomical transverse joint plane and to displace the femoral component anteriorly with respect to the natural anatomical distal femur. The prosthetic knee joint is stable in extension but unstable in high flexion, e.g. 90° flexion, because of the unnatural shortening of the collateral ligament length in high flexion resulting from the uncompensated bone removal in the posterior region of the distal femur effected in preparation for implantation of the revision femoral component.

SUMMARY OF THE INVENTION

It is an object of the present invention to provide a method for replacing a previously implanted total knee prosthesis while retaining the lateral and medial collateral ligaments intact and functional, the practice of which results in a revised prosthetic knee joint that is stable in extension and flexion and affords a relative movement in use between joint components that is similar to that in the natural human knee.

These and other objects are achieved with a novel method for surgically replacing in a patient a previously implanted knee joint prosthesis comprising a first femoral component and a first tibial component with a revision knee joint prosthesis comprising a second femoral component and a second tibial component while retaining the lateral and medial collateral ligaments intact and functional, with each of said first and second femoral components and first and second tibial components comprising a spaced pair of bearing members adapted to fit when implanted against the surgically prepared distal femur and proximal tibia, respectively, said first femoral component bearing members being adapted for mutual articulation with said first tibial component bearing members and said second femoral component bearing members being adapted for mutual non-linked articulation with said second tibial component bearing members, and the bearing members of said first and second femoral components including a distal portion adapted to contact the associated tibial component bearing member when the prosthetic knee joint is in extension and a posterior portion adapted to contact the associated tibial component bearing member when the prosthetic knee joint is in flexion, comprising the steps of (a) selecting a second tibial component;
(b) selecting a second femoral component having bearing members with thicker distal and posterior portions than the bearing members of said first femoral component;
(c) removing said first femoral component and said first tibial component from the body of the patient;
(d) cutting the distal end of the patient's femur and the proximal end of the patient's tibia to prepare said femur and tibia to fit closely with said second femoral component and said second tibial component upon the implantation thereof; and
(e) implanting said second femoral component and said second tibial component at the distal end of the patient's femur and the proximal end of the patient's tibia, respectively, with the dimensions of the bearing members of said second femoral component and said second tibial component being selected so that the natural anatomic transverse joint plane and collateral ligamentous balance are restored in extension and flexion of the prosthetic knee joint. Usually, the second tibial component will have thicker bearing members than the first tibial component.

In a preferred embodiment of the above novel method, the cutting of the distal end of the patient's femur in step (d) comprises making a first horizontal planar cut across the distal end of the femur and then making two additional planar cuts at obtuse angles to said first planar cut and perpendicular to anterior-posterior planes, with one of said additional cuts being in the anterior region of the distal femur and the other of said additional cuts being in the posterior region of the distal femur, and said three planar cuts are adapted to fit closely with three corresponding planar surfaces of said second femoral component.

The present invention also comprises certain items of instrumentation adapted for use in the preparation of the distal end of a patient's femur for the implantation of a revision femoral component.

DETAILED DESCRIPTION OF THE INVENTION

The various aspects of the present invention will be described in detail with reference to certain preferred embodiments thereof. Reference to these embodiments does not limit the scope of the invention, which is limited only by the scope of the claims.

In the drawings:

FIG. 1 is a schematic plan view taken in an anterior-posterior plane of an implanted prior art revision knee prosthesis showing the proximal displacement of the transverse joint plane and the anterior displacement of the femoral component;

FIGS. 2 and 2A are schematic plan views taken in an anterior-posterior plane showing how the implantation of the prior art prosthesis of FIG. 1 leads to excessive ligamental laxity and joint instability in flexion of the joint;

FIGS. 9 and 9A are schematic plan views comparable to FIGS. 2 and 2A and showing the beneficial results of the practice of the present invention;

A prior art revision knee prosthesis is shown schematically in FIG. 1. This prosthesis comprises a femoral component 103 secured to the patient's right femur F and a tibial component 105 secured to the patient's right tibia T. The lateral and medial collateral ligaments of the knee joint of FIG. 1 have been preserved intact and funtional. The curved dotted line in FIGS. 1 and 2 represents the shape of the unreacted natural femur. Femoral component 103 and tibial component 105 each comprise a spaced pair of bearing members adapted for mutual non-linked articulation in use. As used herein, the term "non-linked" means that the two components are capable of being fully separated without having to first disassemble or deform one or both of the components or move the components into a relative disposition not encountered in the normal motion of the artificial joint in the patient's body. Use of non-linked femoral and tibial components, together with preservation of the collateral ligaments, is usually a preferred course of action, if feasible, in both primary and revision total knee arthroplasty in order to permit natural movement of the prosthetic knee joint and prevent the development of excessive stresses at prosthesis fixation interfaces.

The disadvantages of utilizing a primary type of femoral component 103 in revision arthroplasty is clearly shown in FIGS. 1, 2 and 2A. Because of the bone loss incurred in the preparation of the distal femur for the implantation of femoral component 103, which bone loss is not compensated for by the shape of said femoral component, the implanted component 103 is shifted proximally (by a distance $D_1$) and anteriorly (by a distance $D_2$) with respect to the natural anatomical distal femur. Accordingly, the transverse joint plane, which is the horizontal plane perpendicular to the plane of FIG. 1 passing through the lateral and medial contact areas between components 103 and 105, is displaced proximally with respect to the normal anatomical transverse joint plane. The natural anatomical length of the patient's right leg and the natural extended length and degree of tension of the collateral ligaments is restored in extension by adjusting the thickness of the revision tibial component bearing members (see FIG. 2 in which only the medial collateral ligament M is visible). However, during substantial flexion of the prosthetic joint (to e.g. 90% flexion as shown in FIG. 2A), the length of the ligaments (and thus also their tension) decreases by a far greater amount ($L_2$) than in the normal anatomic knee ($L_1$). This decrease in ligamental length, which is caused primarily by the bone loss in the distal posterior femur, can lead to detrimental ligamental laxity and joint instability in the flexed revised prosthetic knee joint and further anterior displacement of the femoral component relative to the tibia. Additionally, the fact that the revised knee bends at a non-anatomical hinge axis places unnecessary stresses upon the tibial and femoral component fixation surfaces and leads to unnatural relative motion between said components.

Figures 3, 5:
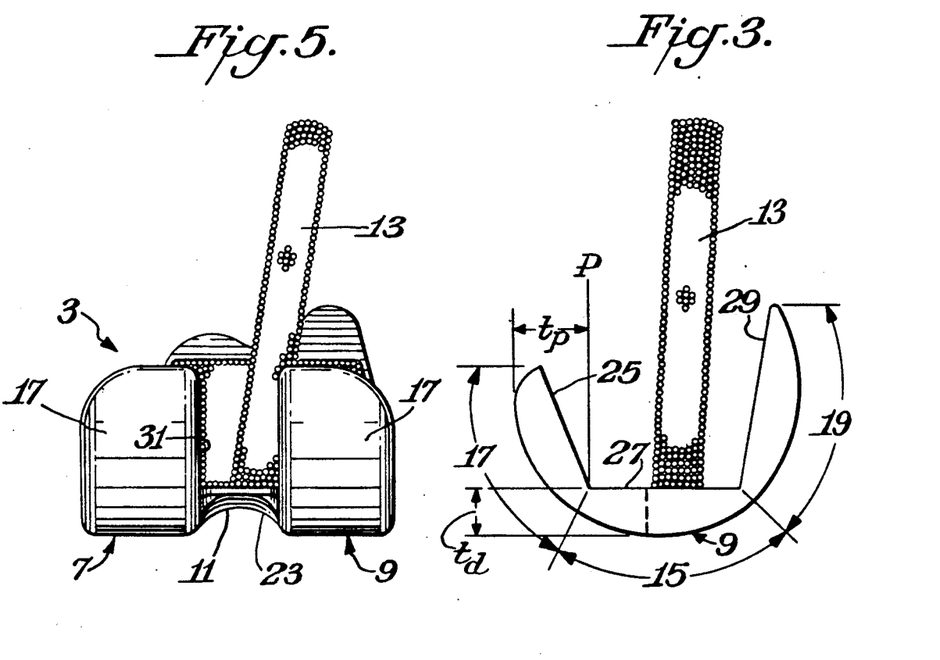
FIGS. 3 to 5 are side, top and rear elevation views, respectively, of a revision femoral component suitable for use in the present invention.
Figure 4:
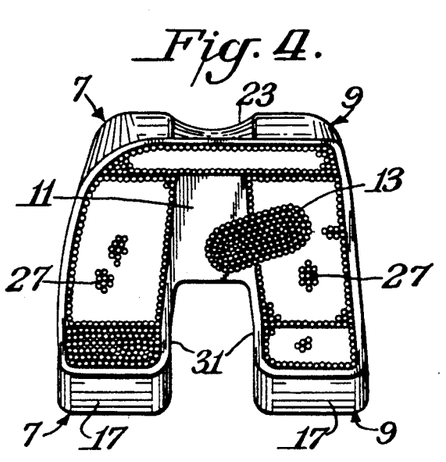

A revision femoral component 3 (right knee) suitable for use in the present invention is shown in FIGS. 3 to 5. Component 3 comprises a spaced pair of bearing members 7 and 9, a portion 11 bridging said bearing members, and a fixation post 13 adapted to fit within the femoral intramedullary canal. As shown in the top plan view of FIG. 4, lateral bearing member 9 is substantially straight while medial bearing member 7 is slightly curved to more readily permit axial rotation of the tibia during flexion. The lower surfaces of bearing members 7 and 9 which contact the tibial component 5 in use are substantially flat when viewed in lateral-medial planes (see FIG. 5). The configurations of members 7 and 9 in top plan and rear plan views are not critical to the practice of the present invention.

Figure 25:
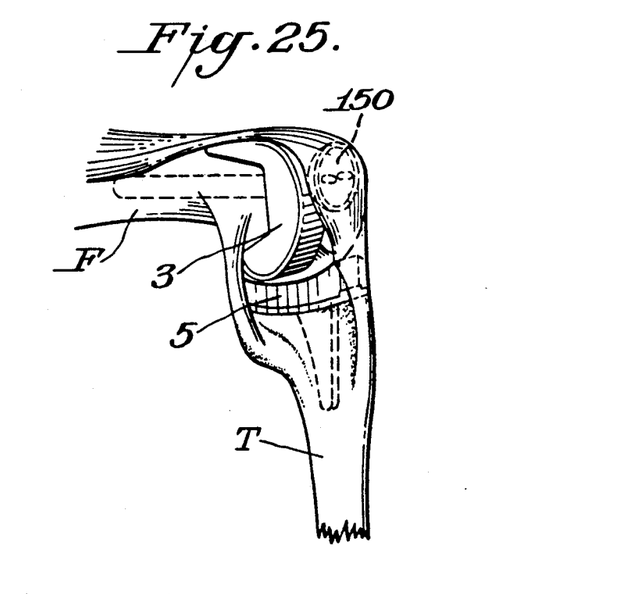
FIGS. 25 is a perspective view of an implanted revision knee prosthesis comprising femoral, tibial and patellar components.

Bearing members 7 and 9 are substantially identical as viewed in anterior-posterior planes such as the plane of FIG. 3, with their lower tibial component-contacting surfaces shaped in such planes to approximate the shape of the natural femoral condylar surfaces. Each of said members contains a distal portion 15 adapted to contact the tibial component when the prosthetic knee joint is in extension and a posterior portion 17 adapted to contact the tibial component when the prosthetic knee joint is in flexion. Preferably, as shown in FIG. 3, each of bearing members 7 and 9 also includes an anterior portion 19 adapted to contact a revision prosthetic patellar component 150 (see FIG. 25) during use of the prosthetic joint.

The anterior and distal portions 19 and 15 of bearing members 7 and 9 and bridging portion 11 form together a track 23 that fits over a cooperating ridge on the patellar component. Track 23 is slightly angled laterally from the vertical. As will be explained later in greater detail, the thickness of distal portion 15 and posterior portion 17 of bearing members 7 and 9 in anterior-posterior planes is of great importance in the practice of the present invention. The thickness of distal bearing portion 15 is measured from horizontal surface 27 downwardly to the tibial component-contacting surface of the distal bearing portion, while the thickness of posterior bearing portion 17 is measured from vertical plane P at the posterior edge of surface 27 posteriorly to the tibial component-contacting surface of the posterior bearing portion.

As is obvious from FIG. 3, it is the lower surfaces of bearing members 7 and 9 that contact the tibial and patellar components in use. The upper surfaces of members 7 and 9 combine with the upper surface of bridging portion 11 to form a three-planed fixation surface for component 3 including a posterior planar surface 25, a distal planar surface 27 and an anterior planar surface 29. (Note that if component 3 contains a slot 31 between members 7 and 9 to allow for preservation of the posterior cruciate ligament, bridging portion 11 does not contribute to posterior planar fixation surface 25.) The planes of each of surfaces 25, 27 and 29 are perpendicular to anterior-posterior planes. Distal fixation surface 27 is horizontal when the prosthetic knee joint is in extension, and fixation surfaces 25 and 29 are oriented at obtuse angles, preferably about 109.5° and 101° respectively, with respect to fixation surface 27. Planar fixation surfaces 25, 27 and 29 are adapted to fit against coinciding surfaces on the prepared distal femur when revision femoral component 3 is implanted. Preferably, a porous coating of the kind disclosed in the above-mentioned copending U.S. patent application Ser. No. 350,130, now U.S. Pat. No. 4,550,448 is provided on most or all of surfaces 25, 27 and 29 and the outer surface of fixation post 13, and the fixation to the femur is accomplished by either tissue ingrowth or cementation. Note that fixation post 13 is angled at about 8° from the vertical in a lateral direction as viewed in the lateral-medial plane of FIG. 5 and is angled at about 2⅛° from the vertical in an anterior direction as viewed in the anterior-posterior plane of FIG. 3.

Figure 6:
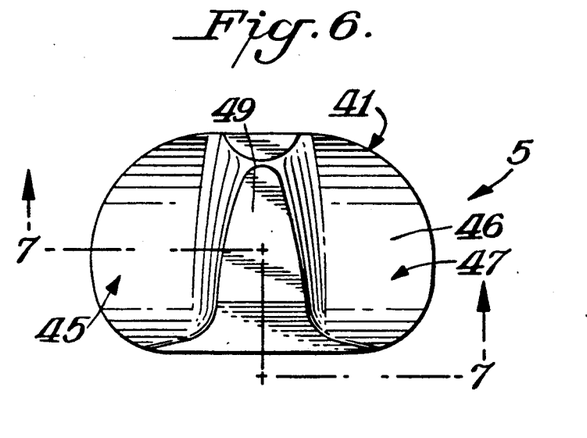
FIGS. 6, 7 and 8 are top, rear and side elevation views, respectively, of a revision tibial component suitable for use in the present invention, with FIG. 7 being partially in half-section.
Figure 7:
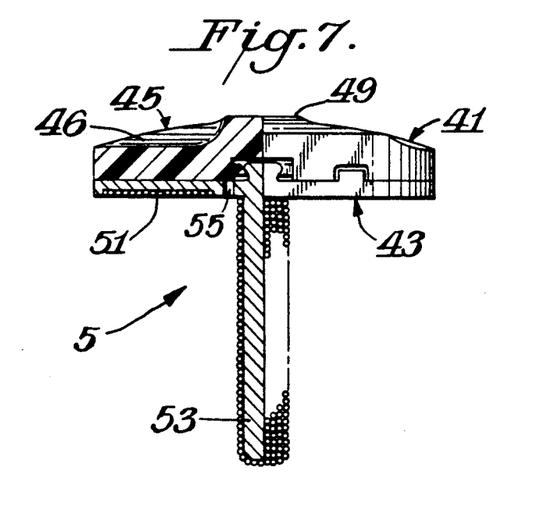
Figure 8:
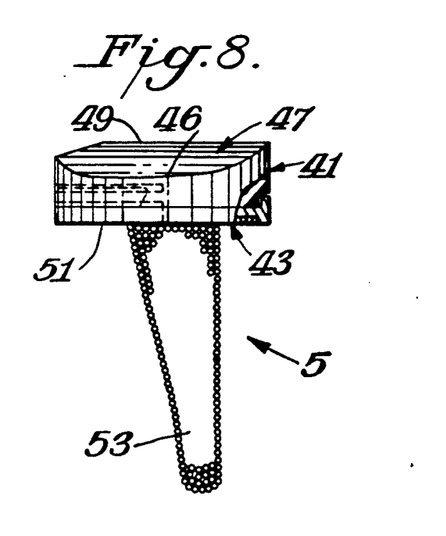
Figure 10:
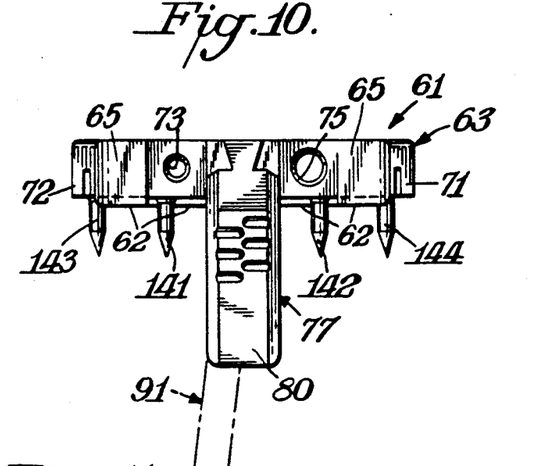
FIGS. 10 to 13 are front, top, side and bottom elevation views, respectively, of a cutting jig suitable for use in the preparation of the distal end of a femur for the implantation of a femoral component of a revision knee prosthesis.
Figure 11:
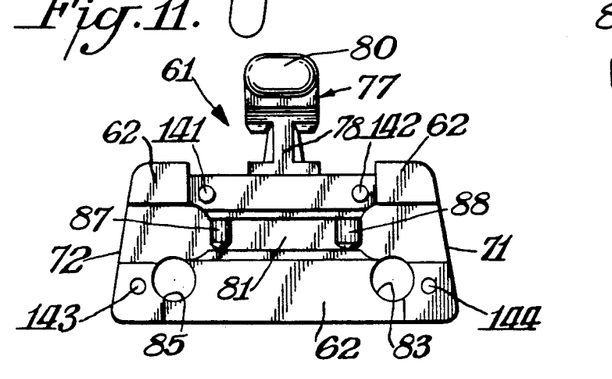
Figure 12:
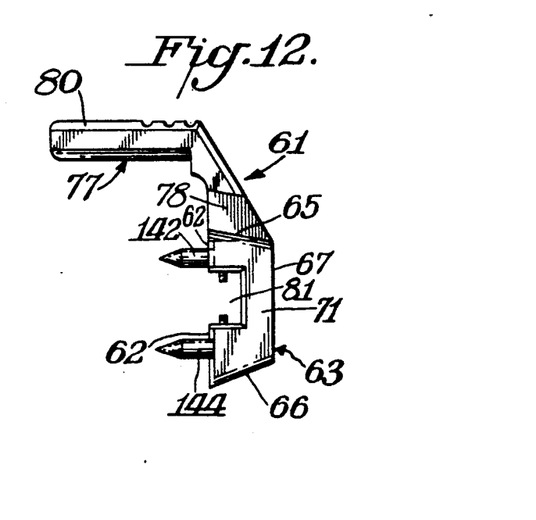
Figure 13:
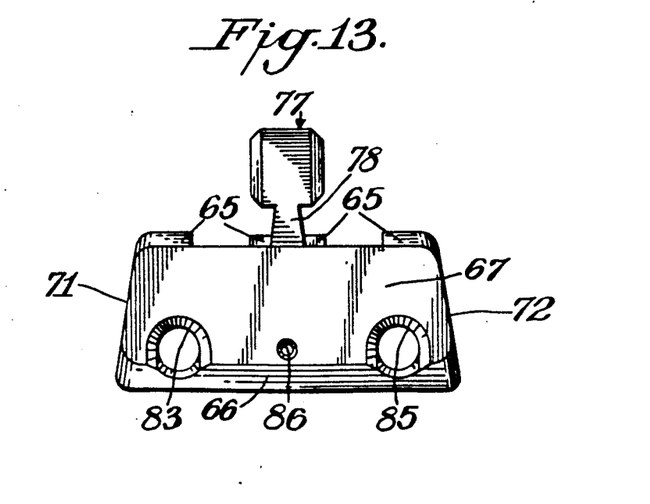

The particular configuration of the revision tibial component is not critical to the practice of the invention. One revision tibial component 5 suitable for use in the present invention, which may be implanted at either the left or right proximal tibia, is shown in FIGS. 6 to 8. Alternatively, a primary type of tibial component such as the one disclosed in the afore-mentioned U.S. patent application Ser. No. 350,130, now U.S. Pat. No. 4,550,448 may be employed. Tibial component 5 is an assembly of a bearing insert 41 secured to a tibial tray 43 by conventional means, e.g. by snap-fit of tray projections within resilient insert openings. The lateral and medial side parts of insert 41 and the two extensions of tray 43 supporting said two side parts form together the two identical bearing members 45 and 47 of component 5, which are separated by raised central member 49. The upper surfaces of bearing members 45 and 47 which contact the femoral bearing members 7 and 9 in use are generally dish-shaped and both include (as shown in FIGS. 7 and 8) a flat central region 46 removed from the anterior and posterior peripheries of said upper surfaces. Region 46 is horizontal as viewed in lateral-medial planes (see FIG. 7) and very slightly sloped (preferably by about 1° to about 2°) in a downward/posterior fashion as viewed in anterior-posterior planes (see FIG. 8).

The lower surface 51 of tibial tray 43 is flat and adapted to fit against a coinciding horizontal surface on the prepared proximal tibia when revision tibial component 5 is implanted. Tibial tray 43 includes a fixation peg 53, and a series of slots, e.g. 55, surrounding peg 53 to facilitate removal of the tibial component, if necessary (see said copending U.S. patent application Ser. No. 350,130, now U.S. Pat. No. 4,550,448). If preservation of the posterior cruciate ligament is desired, tibial component 5 is provided with a posterior slot between bearing members 45 and 47 and underlying the slot 31 of component 3 at extension of the prosthetic joint. Preferably, a porous coating of the kind disclosed in the above-mentioned copending U.S. patent application Ser. No. 350,130, now U.S. Pat. No. 4,550,448 is provided on most or all of surface 51 and the outer surface of fixation peg 53, and the fixation to the tibia is accomplished by either tissue ingrowth or cementation.

Femoral component 3 and tibial tray 43 are preferably made of a corrosion resistant surgical implant alloy, e.g. titanium or a cobalt-chromium-molybdenum alloy (e.g. Vitallium (Howmedica, Inc.; New York, N.Y.)) and tibial bearing insert 41 is preferably made of a biologically compatible high density polymer such as high molecular weight polyethylene. Preferably, component 3 and tray 43 are made by casting (followed by addition of the porous coating by sintering) and insert 41 is made by machining.

The beneficial results stemming from the practice of the present invention can be readily understood by comparing the schematic drawings of FIGS. 2 and 2A with further reference to FIG. 3. On the femoral side, the ultimate goal is to substantially restore the anatomical geometry of the distal end of the patient's pre-existing natural femur. In order to compensate for the distal femur bone loss occuring during the revision arthroplasty, a revision femoral component 3 is selected in which the distal bearing portion 15 is thicker (as measured from horizontal surface 27 downwardly to the tibial component-contacting surface) than the corresponding distal bearing portion in the primary femoral component being replaced and the posterior bearing portion 17 is thicker (as measured from vertical plane P at the posterior edge of surface 27 posteriorly to the tibial component-contacting surface) than the corresponding posterior bearing portion in said primary femoral component. The bearing members of the tibial component 5 will typically have roughly the same thickness as in the primary tibial component being replaced, although some increase in thickness is usually necessary to compensate for the proximal tibia bone loss involved in the revision arthroplasty. When components 3 and 5 are properly selected, the natural anatomical transverse joint plane, collateral ligament length and collateral ligament tension and balance are essentially restored in extension and throughout the full range of intended flexion of the prosthetic joint (typically 0° to 120° of flexion). As a result, the prosthetic knee joint is stable in extension and flexion without the relative motion of the femoral and tibial components being excessively constrained, the revision prosthetic knee is able to reproduce the motion of the normal anatomical knee, and stresses at fixation interfaces are minimized.

In the present application, when it is said that a bearing member or bearing member portion of one prosthetic component is thicker or has greater thickness than the corresponding member or portion of another prosthetic component, it is meant that the bearing member or bearing member portion of the one component has a greater mean thickness (as determined over the full extent of the member or portion as viewed in anterior/posterior planes) than has the corresponding member or portion of the other component. The thickness of femoral bearing member portions 15 and tibial bearing members 45 and 47 includes the thickness of any fixation coatings or layers on surfaces 27 and 51.

In the surgical procedure for implanting the revision femoral and tibial components according to the present invention, much of the instrumentation disclosed in the copending, commonly assigned U.S. patent application Ser. No. 350,013, filed Feb. 18, 1982, entitled "Prosthetic Knee Implantation", now U.S. Pat. No. 4,646,729 can be employed. Said copending U.S. patent application is incorporated herein in its entirety by reference. In addition, instrumentation particularly adapted for use in revision knee arthroplasty, including the instrumentation illustrated in FIGS. 10 to 16, 26 and 27 of the present application, can also be beneficially utilized.

A revision cutting jig 61 highly suitable for use in the preparation of the distal end of the right or left femur in revision arthroplasty is shown in FIGS. 10 to 13. As is best seen in the side view of FIG. 12, cutting jig 61 includes a body portion 63 having substantially the shape of a trapezoidal prism defined by distal base face 67, proximal base face 62 parallel to face 67, anterior side cutting face 65 and posterior side cutting face 66. For reasons that will become clear when the use of cutting jig 61 is described below, cutting faces 65 and 66 form obtuse angles with distal face 67 and diverge from one another in the proximal direction (i.e. from face 67 to face 62). Jig 61 also includes means on proximal face 62, e.g. teeth 141, 142, 143 and 144 projecting from recessed regions on face 62, for temporarily securing jig 61 to the distal end of the patient's femur; means within body portion 63, e.g. dovetail slot 81 open at proximal face 62 and the two end faces 71 and 72 of body portion 63, for the connection to said body portion of a cylindrical rod (described below) adapted to be positioned within the intramedullary canal of the femur; means, e.g. holes 83 and 85 through body portion 63, for the releasable attachment of a distally-extending handle to said body portion; means, e.g. holes 73 and 75 commencing at recessed regions on anterior cutting face 65 and opening into dovetail slot 81, for the releasable attachment of an anteriorly-extending pin holder alignment guide to body portion 63; and a dog-legged tongue 77 extending from anterior cutting face 65. Note that holes 73 and 75 are of different sizes so that the correct position of the pin holder alignment guide on jig 61 cannot be improperly reversed. Tongue 77 includes two sections 78 and 80, with section 80 extending in the proximal direction to the free end of tongue 77 being perpendicular to the planes of base faces 62 and 67. Jig 61 is also provided with a depression 86 in distal face 67 which is adapted to receive a corresponding pin on the distally-extending handle so as to improve the stability of the attachment of said handle to jig 61.

Figure 14:
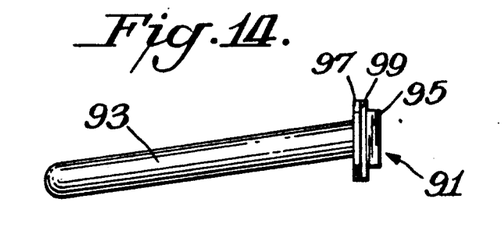
FIGS. 14, 15 and 16 are front, side and bottom elevation views, respectively, of an intramedullary rod adapted for use with the cutting jig of FIGS. 10 to 13.
Figure 15:
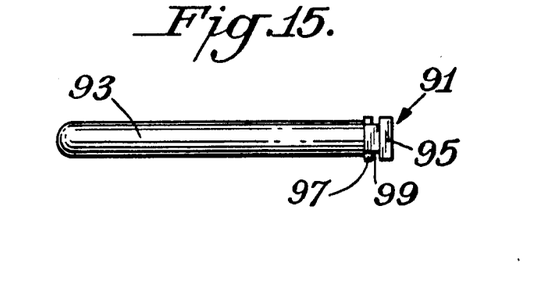
Figure 16:
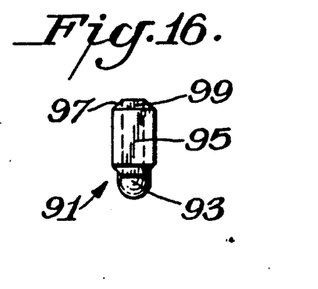

A cylindrical intramedullary rod 91 adapted for use in combination with revision cutting jig 61 is shown in FIGS. 14 to 16. Rod 91 comprises a main cylindrical body portion 93 adapted to be positioned within the intramedullary canal of the patient's femur, a pair of flanges 95 and 97 at the distal end of rod 91, and a reduced portion 99 between flanges 95 and 97. Rod 91 is adapted to be connected to cutting jig 61 by sliding the distal end of rod 91 into dovetail slot 81, with the two ridge-like projections in slot 81 (see FIGS. 11 and 12) received within reduced portion 99 to prevent the escape of said distal end through the opening of slot 81 at face 62 (from right to left in FIG. 12). When cutting jig 61 and intramedullary rod 91 are further combined with a pin holder alignment guide, movement of rod 91 in a lateral or medial direction, i.e. into or out of the plane of FIG. 12, can be limited or prevented by assuring that the fixation pegs of the pin holder alignment guide (which are received within holes 73 and 75 in body portion 63 with the alignment guide is attached to jig 61) are long enough to extend into the dovetail slot 81 and thereby restrict the movement of flange 95 of rod 91. Note that in the embodiment of cutting jig 61 shown in FIGS. 10 to 13 recesses 87 and 88 are provided in the distal wall of slot 81 to accomodate portions of the two pin holder alignment guide fixation pegs. When the cutting jig 61 and intramedullary rod 91 shown in FIGS. 10 to 16 are connected as described above, cylindrical body portion 93 of the rod is angled laterally at an angle of about 8° from a direction perpendicular to the base face 62 of jig 61 to approximate the natural anatomical femoral valgus (note rod 91 shown in phantom in FIG. 10). Intramedullary rod 91 may be used in the preparation of the distal end of either the left or right femur for the implantation of a femoral component simply by reversing the position of its distal end in slot 81.

Figures 26, 27:
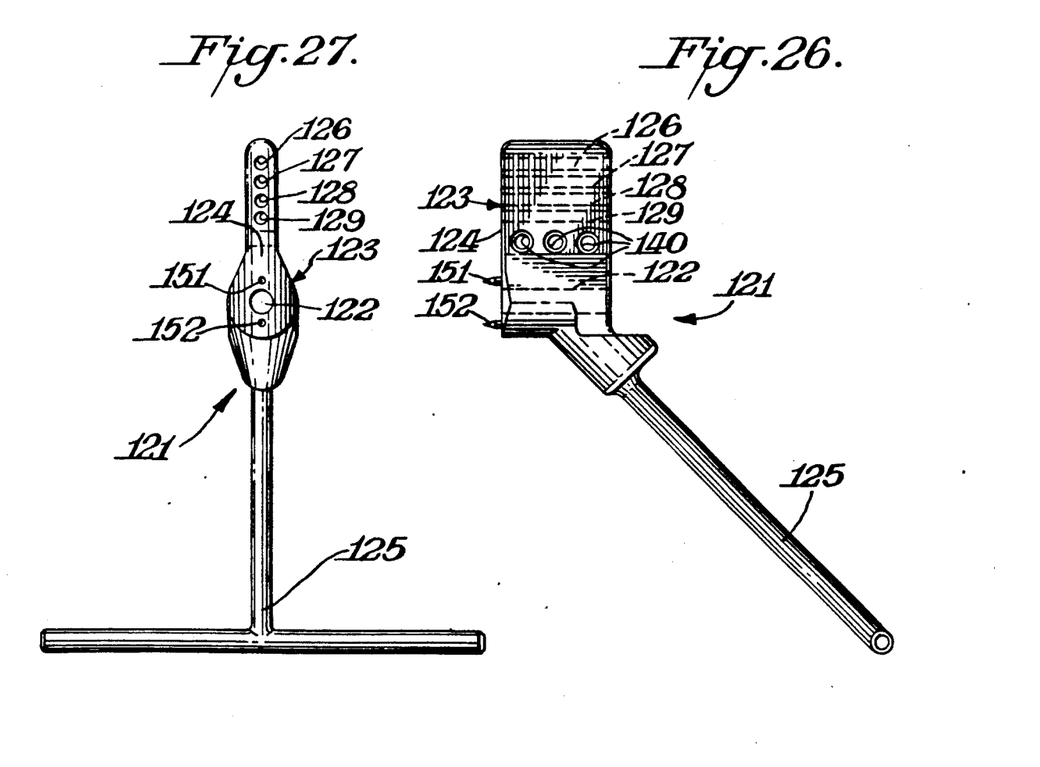
FIGS. 26 and 27 are side and top elevation views, respectively, of a drill guide suitable for use in the preparation of the distal end of a femur for the implantation of a femoral component of a revision knee prosthesis.

An intercondylar drill guide 121 comprising a "T-bar" handle 125 and a body portion 123 with a proximal face 124 is shown in FIGS. 26 and 27. Body portion 123 is provided with a through bore 122 for the guidance of a drill and a plurality of through bores, e.g. 126 to 129, parallel to bore 122 for the receipt of a straight alignment pin. Drill guide 121 also includes means on proximal face 124 for temporarily securing the drill guide to the distal end of a patient's femur, e.g. teeth 151 and 152. Preferably, teeth 151 and 152 are coplanar with bores 122 and 126 to 129. It is also preferred that proximal face 124 not be flat, but instead slightly rounded transversely to adapt to the intercondylar notch. Most preferably, proximal face 124 has a constant radius of curvature from one end to the other as viewed in transverse cross-sections through body portion 123 taken perpendicular to the plane of FIG. 27. Drill guide 121 may also be provided with a plurality of through bores, e.g. 140, to reduce its weight.

Figures 17, 18:
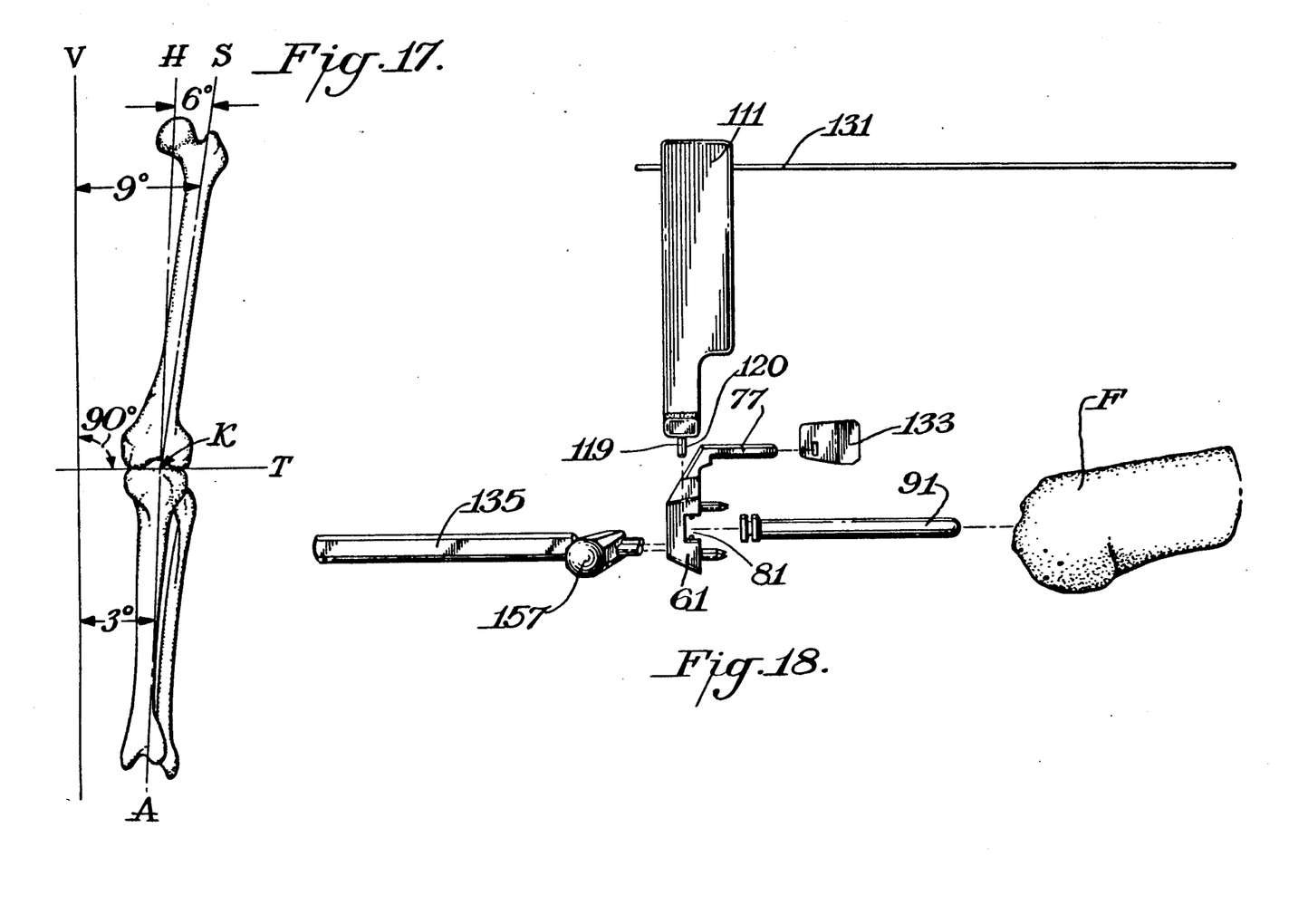
FIG. 17 depicts various anatomical references of interest (left leg, front view) in relation to the present invention.
FIGS. 18 to 24 illustrate the preparation of the distal end of a patient's femur for the implantation of the revision femoral component of FIGS. 3 to 5.

In the preferred surgical procedure for implanting revision femoral component 3 and revision tibial component 5, a number of natural anatomical landmarks are used as references (see FIG. 17, which is a front plan view of the left leg in one-legged stance at extension). The mechanical axis H of the leg is a straight line through the center of the ankle A, the center of the knee K and the center of the femoral head. In normal adult humans, mechanical axis H is oriented at a 3° angle with respect to vertical axis V. Transverse joint plane T is a horizontal plane perpendicular to the plane of FIG. 17 drawn through the lateral and medial femur/tibia contact areas and the center of the knee K. Axis S is the axis of the femoral shaft. Axes H, V and S are all in the same lateral-medial plane. It is necessary in each individual case to determine the correct femoral valgus for that individual by measuring the angle between axes H and S by X-ray and then adding 3 degrees for the inclination of mechanical axis H to the vertical. In most cases this will give 9° of femoral valgus. A number of basic bone cuts are required to align and seat revision components 3 and 5. Accurate alignment is important to insure that horizontal surfaces 27 and 51 are parallel to the natural anatomic transverse plane of the knee and perpendicular to the lateral-medial planes (e.g. plane of FIG. 17). Malalignment can lead to instability, ligamental unbalance and excessive stresses at fixation interfaces. As used throughout this application the terms anterior, posterior, up, down, vertical, horizontal, etc., which connote a certain direction refer to the positions of the femoral and tibial components at extension unless the context clearly indicates otherwise.

The incision for revision total knee arthroplasty is carefully chosen based upon the scars that are present. Since most prior prostheses will have used an anterior or parapatella incision, the old scar should be utilized and the incision extended more proximally. It is important to mobilize completely the quadriceps mechanism from the scarred synovium before proceeding. It is also important to carry the incision far enough proximally so that the patella can be completely dislocated, everted, and the knee flexed to 90 degrees without putting excessive tension on the patellar tendon at the tibial tubercle. The primary component parts which are to be revised are then removed starting with the femoral component. Care must be exercised to avoid fracture of residual bone and to remove as little remaining bone stock as possible. High speed cement and metal cutting burrs are helpful. Often, however, the component parts are loose and can be easily removed. In the case of metal tibial trays in which the stem is not loose, the tray around the central stem can be cut with a high-speed diamond cutting disc. This gives access to the cement-bone interface of the central peg with minimum tibial bone loss. Following the removal of the components, the knee is completely debrided to include loose cement, cement in keying holes, and the posterior aspect of the joint.

Next, a number of instruments are assembled for aligning the distal femoral cut (see FIG. 18). Intramedullary rod 91, which can be positioned relative to the revision cutting jig 61 with either a right or left valgus angle, is passed into the dovetail slot 81 in the jig 61. Rod 91 is centered between the two holes 73 and 75 in the body portion 63 of jig 61. A pin holder alignment guide of the type disclosed in copending application Ser. No. 350,013, now U.S. Pat. No. 4,646,729 can be beneficially employed in the practice of the present invention. The unequally-sized fixation pegs 119 and 120 of the pin holder alignment guide 111 (carrying a straight guide pin 131 at the proper femoral valgus setting) are inserted into holes 73 and 75 with pin holder 111 extending anteriorly of jig 61. Pegs 119 and 120 of pin holder 111 should embrace flange 95 of intramedullary rod 91 when pin holder 111 is fully seated so as to lock the rod 91 in place. A transverse cutting jig 133 of the type disclosed in said copending application Ser. No. 350,013, now U.S. Pat. No. 4,646,729 is then slid over the anterior tongue 77 of cutting jig 61 and handle 135, which is used to control alignment of the jig 61, is then inserted into the holes 83 and 85 and the depression 86 in the body portion 63 of the cutting jig 61 with the handle extending distally of jig 61. Note that the anterior direction is towards the top of FIG. 18.

Figure 19:
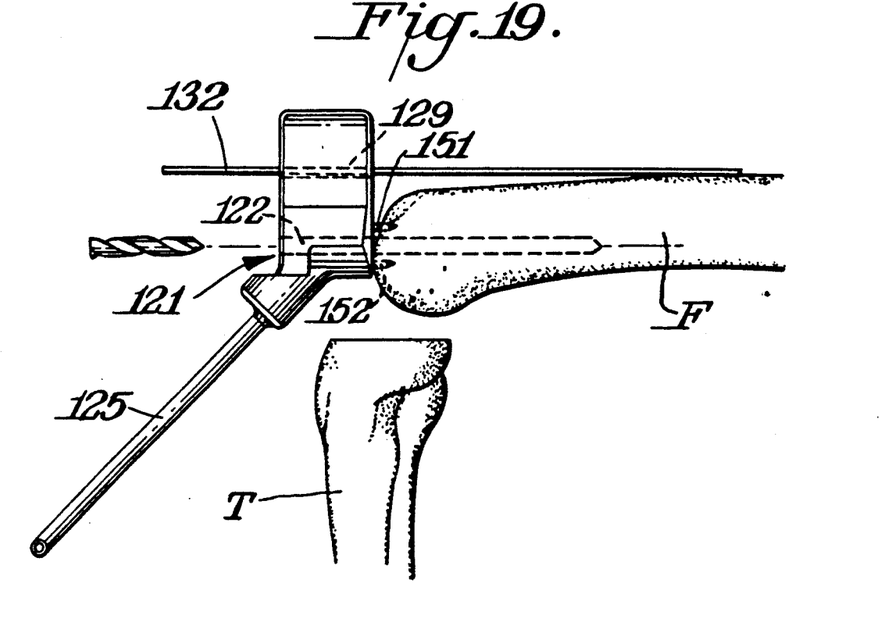

With the knee flexed at 90 degrees, a drill hole (e.g. 5/16 in. diameter) is placed in the center of the femoral intercondylar notch using the drill guide 121 which references off the anterior femoral cortex (see FIG. 19). To insure proper alignment of this drill hole, an axial alignment pin 132 is passed through one of the parallel bores 126 to 129 in body portion 123 and under the quadriceps mechanism paralleling the anterior femur. The anterior-posterior position of this drill hole is not critical to the angular orientation of the distal femoral cut, but it will be important to the anterior-posterior position of the femoral component 3.

Figure 20:
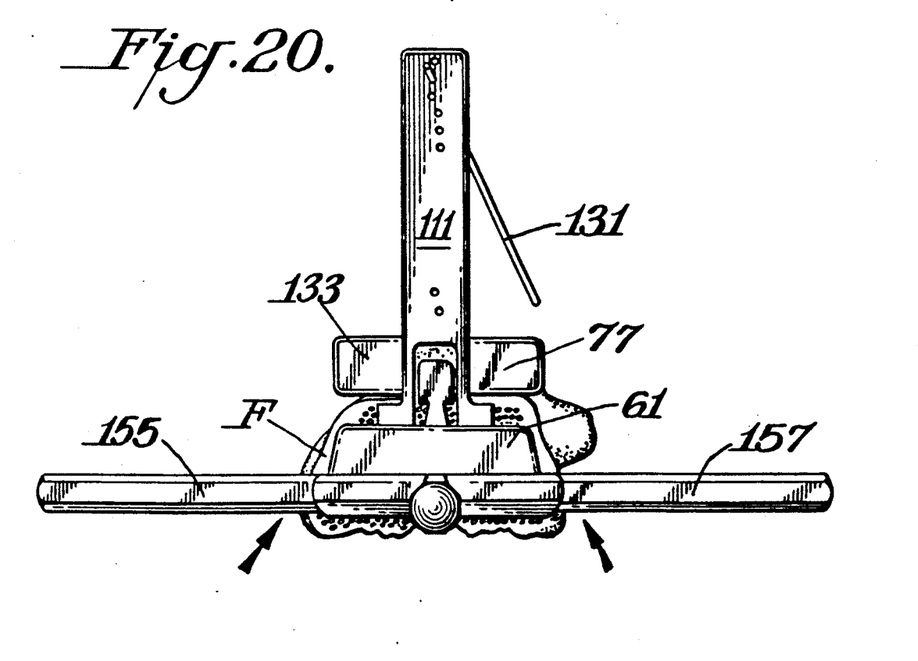

Next, the assembly shown in exploded view in FIG. 18 is mounted on the distal end of the femur F by inserting intramedullary rod 91 through the previously formed drill hole into the femoral intramedullary canal. Cutting jig 61 is pressed forward until teeth 141, 142, 143 and 144 just contact the distal femoral surface. Cutting jig 61 is then aligned in an axial rotational aspect by aligning the medial arm 155 and lateral arm 157 of "T-bar" handle 135 to be parallel to the epicondyles (see FIG. 20).

The pin holder alignment guide 111 is used to establish proper varus-valgus and flexion-extension alignments of the cuts at the distal end of the femur F. Correct axial alignment is achieved when the alignment guide pin 131 is parallel to the femoral shaft axis in both the anterior and lateral views (see FIGS. 21 and 22). Care must be exercised to be certain that, while varus-valgus and flexion-extension alignments are being achieved, axial rotational alignment is not lost.

With the alignment of cutting jig 61 assured in all three aspects, cutting jig 61 is locked in place by tapping teeth 141, 142, 143 and 144 into the distal end of the femur F. Then, jig 133 is slid proximally or distally on arm 80 of tongue 77 until it defines (with its planar distal face) a suitable plane for the revision distal planar cut (rotation of jig 133 with respect to arm 80 is prevented by the shape of arm 80 nd the bore in jig 133 receiving it). Jig 133 should be positioned so that only as much bone is respected to correct the plane of the original distal femoral cut as necessary (see FIG. 23). It is seldom possible to cut into virgin bone completely, and under no circumstances should the cut be made proximal to the femoral attachment of the collateral ligaments. The goal is simply to have a properly aligned and sufficiently stable base to proceed to the next step.

Figures 21, 23:
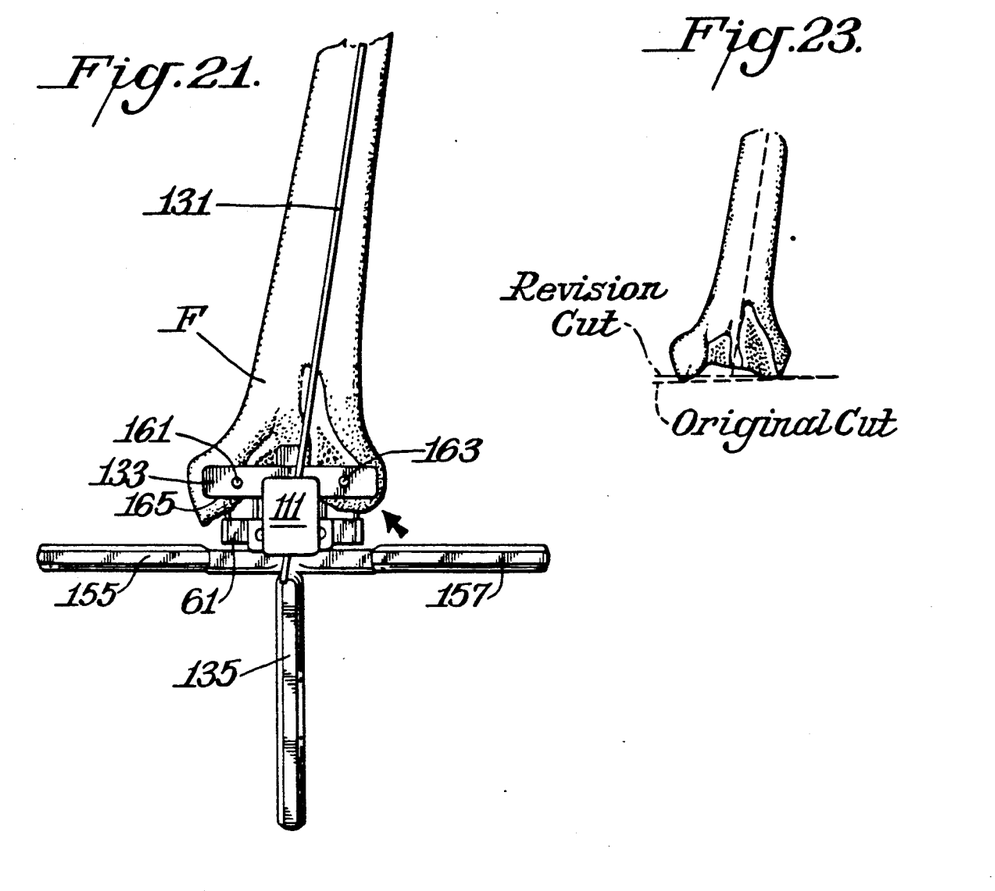

With the level and plane of the distal femoral cut determined, two e.g. ⅛ inch drill pins are passed through holes 161 and 163 in jig 133, thereby locking jig 133 onto the distal femur. The cutting jig 61 is then removed, leaving jig 133 locked onto the femur. The distal femur is then recut, preferably using a piston-grip, end-cutting oscillating saw. It is important that the surgeon pay close attention to maintaining the saw blade flat against the distal cutting face 165 of jig 133 in order to achieve a precise cut. Once the cut has been completed, the flat surface of any of the cutting jig can be used to check that the surface is true. The jig 133 is then removed. The two e.g. ⅛ inch drill pins are left in place as additional medial-lateral and rotational references for positioning jig 61 for making the anterior and posterior cuts. These two pins will of course have to be removed before making the anterior cut.

At this point it should be noted that the surgeon will advantageously have available a plurality of femoral components 3 of different sizes, e.g. small medium, large, to account for anatomical size differentials at the distal end of the femur from patient to patient. At certain fixed sizes, e.g. medium and large, the surgeon will also advantageously be provided with a plurality of femoral components 3 of different bearing member portion thicknesses, for reasons to be discussed below. The surgeon will be provided with a plurality of revision cutting jigs 61 of different sizes, each being adapted for use in the preparation of the femur for the implantation of one of the different sizes of revision femoral components 3. The proper size of cutting jig 61 to be used can usually be selected by eye. In case of doubt, the larger cutting jig should be used first since it will then be possible to subsequently recut the distal femur with the next smaller cutting jig if necessary.

Figure 22:
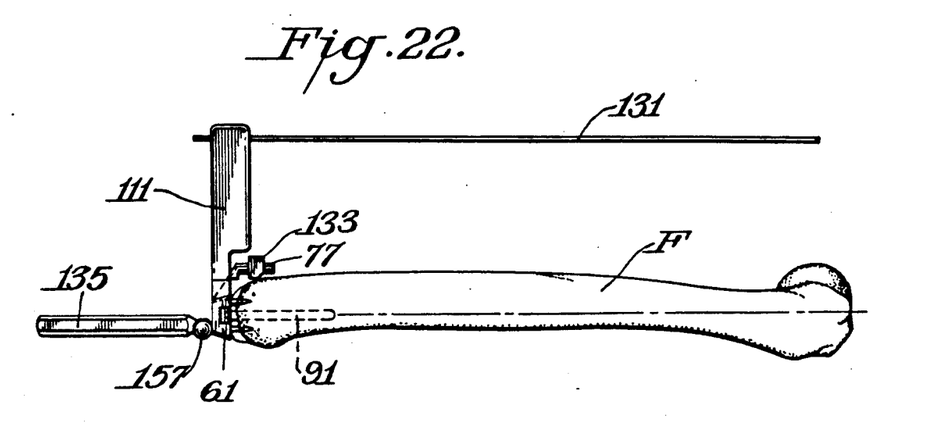
Figure 24:
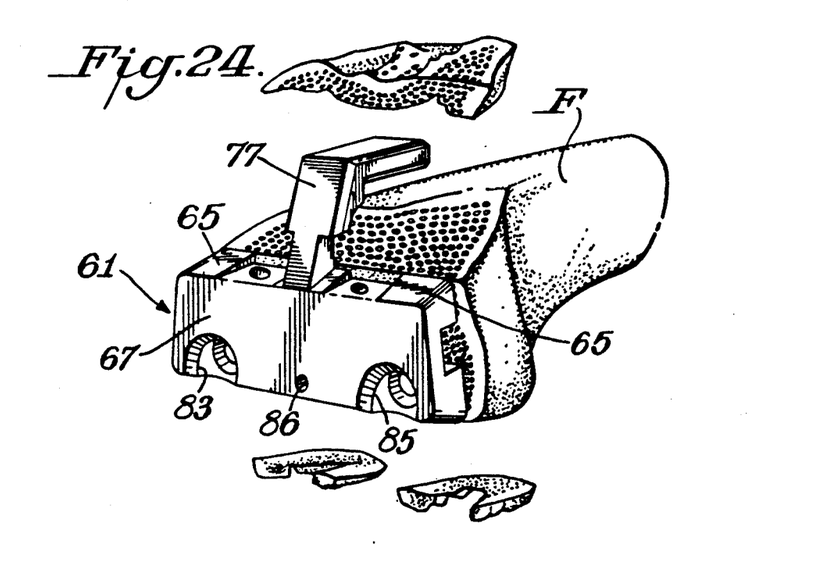

The revision cutting jig 61, intramedullary rod 91, pin holder alignment guide 111, guide pin 131 and "T-bar" handle 135 (but not jig 133) are reassembled as shown in FIGS. 18 and 22 and reinserted into the intramedullary canal. If necessary in a case of severe bone destruction or abnormality, a suitable tab (not shown in the figures) adapted for referencing off the anterior complex may be temporarily slipped onto arm 80 to assist in the determination of the proper anterior-posterior position of jig 61. Arms 155 and 157 of handle 135 are again aligned with the epicondyles and the teeth on jig 61 are then tapped into the bone until the proximal face 62 of jig 61 is flush against the freshly recut distal femur. The proper position of guide pin 131 in both anterior and lateral views should be verified and the pin holder 111, guide pin 131 and handle 135 then removed. At this point the anterior and posterior regions of the distal femur are cut, using anterior side and posterior side cutting faces 65 and 66 of cutting jig 61 as guides (see FIG. 24). These two bone cuts are then checked for flatness.

The preparation of the proximal end of the patient's tibia for trial reduction and implantation of a tibial component 5 is a relatively simple matter, involving only a single horizontal transverse cut across the entire bone. The method and instrumentation described in said copending U.S. patent application Ser. No. 350,013, now U.S. Pat. No. 4,646,729 which prior U.S. patent application is incorporated herein in its entirety by reference, are preferably employed in preparing the tibia for initial trial reduction with only one significant change. The revision cutting jig 61 is left in place on the distal femur until the transverse tibial cutting jig 133 has been locked into place on the tibia and the pin holder alignment guide 111, guide pins and femoral spacer/tensor jig have been removed. In use, the femoral spacer/tensor jig fits into holes 83 and 85 in the body portion of jig 61 rather than into a pair of holes in the prepared femur.

For use in implantation, the surgeon is preferably provided with revision femoral components and revision tibial components having a plurality of different sizes adapted to match the different transverse cross-sectional dimensions of the femurs and tibias of different patients. At each size of tibial component, a range of bearing member thicknesses (e.g. 10 mm. to 22 mm.) is available. Additionally, at least at each of certain larger sizes, femoral components having a plurality of different distal bearing portion thicknesses (e.g. 11 mm. to 15 mm. maximum thickness $t_d$ (see FIG. 3)) and constant posterior bearing portion thickness (e.g. 18 mm. maximum thickness $t_p$) are available. In all of the revision femoral components, the tibial component-contacting lower surface of the bearing members if shaped, in the anterior-posterior aspect, to resemble the shape of the anatomical femoral condylar surfaces. The surgeon is also provided with a set of trial femoral components, tibial trays, tibial bearing inserts and patellar components, having the same dimensions as the set of components, trays and inserts intended for ultimate implantation, for use in trial reductions of the prosthetic joint.

Initial trial reduction is commenced with a tibial positioning/fixation jig (described in said copending application Ser. No. 350,013, now U.S. Pat. No. 4,646,729) mounted in place on the tibia. If this jig is not stable, the appropriately-sized hole to receive fixation peg 53 is cut in the proximal tibia, e.g. with an osteotome, and a trial tibial tray utilized instead. In general, trial reduction is carried out in substantially the same manner as described in said application Ser. No. 350,013, now U.S. Pat. No. 4,646,729. However, in the present (revision) case, adjustments can be made in the thickness of both the tibial and femoral bearing members. Such adjustments are continued until satisfactory ligamental balance is obtained in both extension and in high flexion. Of course, one important advantage of the practice of the present invention is that it allows for stable trial reduction to take place through variation in the thickness of the femoral component bearing members as well as in the thickness of the tibial component bearing members.

During the initial trial reduction, a variety of instability problems may be encountered. These require choices among the components available to achieve optimal balance of the soft tissue envelope of the knee. There are basically three possibilities for flexion and for extension stability: too loose, too tight or "just right". This gives nine possible combination of which only "just right" for stability in extension and "just right" for stability in flexion is acceptable. Adjustments for alleviating the problems associated with the eight other potential conditions are outlined below for the situation in which a femoral component size is being used for which the surgeon has available a plurality of femoral components with the same posterior bearing portion thickness and varying distal bearing portion thickness:

| | ADJUSTMENT | | |
|---|---|---|---|
| CONDITION | FEMORAL SIDE | TIBIAL SIDE | RATIONALE |
| (1) Extension Too Loose Flexion Too Loose | Nothing | Thicker Plateau | Thicker tibial plateau will increase stability in both flexion and extension. |
| (2) Extension Too Loose Flexion Too Tight | Thicker femoral component | Thinner plateau | Thicker femoral component increases stability in extension, allowing thinner tibial component to loosen ligaments in flexion. |
| (3) Extension Too Loose Flexion Just Right | Thicker femoral component | Nothing | Thicker femoral component increases stability in extension only. |
| (4) Extension Too Tight Flexion Too Loose | Thinner femoral component or additional femoral resection | Thicker plateau | Thinner femoral component reduces tension in extension permitting use of thicker plateau to increase stability in flexion. |

-continued

| CONDITION | ADJUSTMENT | | RATIONALE |
|---|---|---|---|
| | FEMORAL SIDE | TIBIAL SIDE | |
| (5) Extension Too Tight Flexion Too Tight | Nothing | Thinner plateau or additional tibial resection | Opposite of condition #1. Thinner tibial plateau will decrease tightness in both flexion and extension. |
| (6) Extension Too Tight Flexion Just Right | Thinner femoral component or additional femoral resection | Nothing | Thinner femoral component will decrease tightness in extension but not affect stability in flexion. |
| (7) Extension Just Right Flexion Too Loose | Thinner femoral component or additional femoral resection | Thicker tibial plateau | Same rationale as condition #4. |
| (8) Extension Just Right Flexion Too Tight | Thicker femoral component | Thinner tibial plateau | Same rationale as condition #2. |

It must be recognized that the application of any adjustment may generate another condition which must in turn be alleviated. However, each adjustment should lead closer to the desired final result of stability and soft tissue balance throughout the range of motion. Prior to component implantation, a final trial reduction using actual femoral and tibial components and including reduction of the patella with an actual patellar component should be performed.

In implanting the selected revision components 3, 5 and 150 by cementation (component 150 is the revision patellar component—see FIG. 25), the components are sequentially implanted inserting the tibial component first, followed by the femoral and patellar components. Prior to the actual seating of the components, it is preferred to control bleeding, particularly from those areas to which access would be difficult with the revision knee prosthesis in place. The lateral geniculate artery in the posterior-lateral corner, the vessels around the tibial attachment of the posterior cruciate ligament, and lateral retinacular vessels, particularly if lateral parapatellar release has been performed, are the most important sources of bleeding.

When one is dealing with a hard cortical shell, it should be multiply perforated with a small drill bit. The remaining bone should be meticulously debrided of all soft tissue, and any remaining cancellous bone cleaned with pulsatile lavage to facilitate interdigitalization with the cement. Since the tibia often contains deep holes that must be completely filled with cement, it is preferred to use low viscosity cement for the tibial fixation. The apices of these excavations can be connected to the outside by inserting a 16-guage needle into an ⅛ inch drill hole. As the cement is poured into the tibia, a 20 cc syringe attached to the needle will aspirate air and residual blood which has a tendency to collect at the bottom of these cavities.

After initial insertion of the tibial component and removal of excess cement, the tibial component 5 is held in position until the cement has set. The femoral and patellar components 3 and 150 can be cemented simultaneously. Regular polymethylmetharcylate cement may be used for the femur. The cement can be applied to the bone and prosthesis simultaneously in the early dough phase. Any posterior cavities can be finger packed, but the cement should be applied only to the prosthesis on the posterior planar surface 25. This prevents the cement from running down into the posterior aspect of the joint. Once the prosthesis is fully inserted, excess cement is removed and the knee is fully extended, which locks the femoral component in position until the cement is hardened. The knee is then flexed and any prominent cement can be removed with an osteotome. The patellar component is held to the patella with a patellar clamp until the cement is hardened. The wound is lavaged again and closed in a routine fashion. A dry, sterile compression dressing may be applied. However, we have found, particularly in cases with extensive dissection, that a light compression dressing and immediate postoperative, continuous passive motion has been highly effective in maintaining good range of movement in the revised prosthetic joint.

I claim:

1. A cutting jig for use in the preparation of the distal end of a femur for the implantation of a femoral prosthesis, said cutting jig comprising a body portion having parallel distal and proximal base faces and anterior and posterior side cutting faces diverging form one another in the proximal direction and forming obtuse angles with said distal base face, means on said proximal base face for temporarily securing the jig to the distal end of said femur, means within said body portion for the connection thereto to one end of a rod adapted to be positioned within the intramedullary canal of the femur, said means allowing medial-lateral adjustment of the position of said rod within the cutting jig body, means for the releasable attachment of a handle to said body portion, means for the releasable attachment of a pin holder alignment guide to said body portion, and a tongue extending from said anterior side cutting face, with the section of said tongue furthest from said anterior side cutting face extending in the proximal direction to the free end of the tongue and being substantially perpendicular to the plane of said proximal base face.

2. In combination:
 a cutting jig of claim 1;
 a pin holder alignment guide releasably attached to the body portion of said cutting jig; and
 a cylindrical rod adapted to be positioned within the intramedullary canal of said femur and securely attached to the body portion of said cutting jig as a result of the cooperation of means at the distal end of said cylindrical rod, said pin holder alignment guide and said connection means within the body of said cutting jig.

3. A combination of claim 2 wherein said cylindrical rod is angled laterally at an angle of about 8° from a direction perpendicular to said proximal base face.

4. A cutting jig as set forth in claim 1 wherein said means within said body portion for connection of said rod thereto comprises an open keyway slot in said proximal base face for sliding engagement with a corresponding key at said one end of said rod.

5. A cutting jig as set forth in claim 4 wherein said keyway slot on said proximal base face includes means for preventing said rod from disengaging from said body in the proximal-distal direction.

6. A cutting jig as set forth in claim 4 further including means for limiting sliding movement of said rod within said keyway slot in the medial-lateral direction.

* * * * *